United States Patent [19]

Bombardelli

[11] Patent Number: 5,376,371
[45] Date of Patent: Dec. 27, 1994

[54] COMPOSITIONS FOR TREATING FAT DEPOSITS IN HUMANS

[75] Inventor: Ezio Bombardelli, Milan, Italy

[73] Assignee: Indena S.p.A., Milan, Italy

[21] Appl. No.: 603,141

[22] Filed: Oct. 25, 1990

[30] Foreign Application Priority Data

Oct. 27, 1989 [IT] Italy .................. 22174 A/89

[51] Int. Cl.⁵ ............................. A61K 35/78
[52] U.S. Cl. ...................... 424/195.1; 514/909
[58] Field of Search ............... 424/195.1, 909

[56] References Cited

U.S. PATENT DOCUMENTS

| | | | |
|---|---|---|---|
| 69,414 | 10/1867 | Daniel | 424/195.1 |
| 115,407 | 5/1871 | Wright | 424/195.1 |
| 4,525,359 | 6/1985 | Greenway | 514/653 |
| 4,544,556 | 10/1985 | Fedi | 514/263 |
| 4,588,724 | 5/1986 | Greenway | 514/250 |
| 4,638,095 | 1/1987 | Chang | 568/326 |
| 4,795,638 | 1/1989 | Ayache | 424/195.1 |

OTHER PUBLICATIONS

Castleman M. The Healing Herbs, Rodale Press Emmaus, Pa. 1991, pp. 190–192.
Steinmetz E. F. Codex Vegetabilis 1957 Amsterdam #588, 822, 980, 1011, 1124.
The Merck Index 9th Ed 1976 Merck & Co Rahway N.J. #764, 4929, 8027, 9769, 9771.
Goodman & Gilman, The Pharm. Basis of Therapeutics, 7th Ed 1965 MacMillan Co N.Y. pp. 145–151, 156–157, 177–180.
The Merck Index 10th Ed 1983 Merck & Co. Rahway, N.J. #5271.

Primary Examiner—Jeffrey E. Russel
Assistant Examiner—Ralph Gitomer
Attorney, Agent, or Firm—Mathews, Woodbridge & Collins

[57] ABSTRACT

Pharmaceutical and cosmetic compositions for the treatment of superfluous fat deposits contain (a) vegetable active principles having adenylate cyclase agonistic activity or (b) vegetable active principles having antiphosphodiesterase activity or a combination of the two kinds of active principles (a) and (b).

7 Claims, No Drawings

COMPOSITIONS FOR TREATING FAT DEPOSITS IN HUMANS

The present invention concerns compositions for treating fat deposits in humans.

More particularly, the invention relates to compositions containing (a) vegetable active principles having adenylate cyclase agonistic activity or (b) vegetable active principles having antiphosphodiesterase activity or a combination of the two kinds of active principles (a) and (b).

Obesity is a problem affecting a major and increasing part of western population. The weight reduction in obese subjects may be achieved either by pharmacological means or by selected therapeutic diets: however, in both cases, the more or less dramatic weight reduction does not always give satisfactory results from the aesthetic point of view since the fat deposits in some body areas (particularly thighs, gluteus hips knees) remain unchanged, causing unpleasant physical disproportion with consequent psychological distress of the patient.

The problem of fat deposits affects also some part of the adult female population having normal weight.

In most cases, the pharmaceutical or cosmetic compositions presently available for the treatment of fat deposits do not give the expected results.

It has now been surprisingly found that compositions containing plant extracts or their selected constituents having agonist action on adenylate cyclase and/or extracts or compounds possessing anti-phosphodiesterase activity, accelerate and make the reduction of fatty deposits located in the above cited areas easier thus obtaining significant advantages both in the elimination of physiological aesthetic defects and in the consequence of the forced body weight reduction.

According to the invention, suitable adenylate cyclase agonists are extracts of plants belonging to the Convolvulaceae family, such as *Ipomea hederacea, Ipomea parassitica, Ipomea batata* etc. or belonging to Labiatae family such as *Salvia officinalis, Salvia meltiorrhiza* and *Rosmarinus officinalis*. As far as the antiphosphodiesterase activity is concerned, useful plants are those containing dimeric flavones derived from apigenine skeleton; among these, *Ginkgo biloba, Sequoia sempervirens, Taxus baccata, Selaginella rupestris* etc. can be used as a source of active material. The extracts of these plants or their particular fractions can be used alone or in a mixture in different ratios with adenylate cyclase agonists or with other active principles already used for the same purposes, such as yohimbine isomers.

It is particularly preferred the use of apigenine dimers or corresponding derivatives such as amentoflavone, bilobetine, sciadopitisine, ginkgonetine etc., or flavone dimers having similar structure. It is known that amentoflavone is a powerful inhibitor of phosphodiesterase and other dimers having similar structure also share the same activity.

It has now been found that the combination of these flavones in pure form or of extracts containing them with adenylate cyclase agonists can dramatically decrease fat deposits when topically applied on areas where fats accumulate.

The previously cited Ipomea or Labiatae species extracts are particularly active as adenylate cyclase agonists.

The adenylate cyclase agonistic activity of *Ipomea hederacea, Ipomea batata, Ipomea parassitica, Salvia officinalis, Salvia meltiorrhiza* is shown in Table 1.

TABLE 1

Adenylate cyclase activity of various crude extracts on bovine heart homogenates.

| Substances | Conc. mg/100 µl | Specific Activity |
|---|---|---|
| Control | // | 21.8 + 3.9 |
| Ipomea hederacea | 0.2 | 51.3 + 4.1 |
|  | 0.4 | 58.6 + 0.8 |
| Ipomea parassitica | 0.2 | 32.8 + 2.6 |
|  | 0.4 | 33.7 + 1.5 |
| Ipomea batata | 0.2 | 44.6 + 3.9 |
|  | 0.4 | 56.3 + 4.6 |
| Salvia meltiorrh. | 0.2 | 50.3 + 5.4 |
|  | 0.4 | 57.2 + 4.8 |

The determination of the agonist action of these extracts on adenylate-cyclase was determined according to the method of Kurokawa et al. (Biochim. Biophys. Acta 583,467,1979) using brain, heart homogenates or tumoral cells. Adenylate cyclase activity was assayed on the basis of formation of (3H) cyclic AMP from the (3H) ATP. Activity ratio was expressed as a percentage of the activity with the sample-against the basal activity. As a reference substance, Forskoline, a well known adenylate-cyclase agonist, has been used.

The determination of the phosphodiesterase activity was carried out according to the method of Beretz et al. (Experientia, 34,1054,1977). The method consists in measuring (3H) products resulting from incubation of (3H)-c-AMP with the phosphodiesterase preparation and with an excess of nucleotides. An anion exchange resin was used in a batch process to remove the residual substrate. The inibition of PDE by flavonoids was studied in experiments in which the concentration of c-AMP was held constant at 1 µM. The I-50 (concentration of flavonoid resulting in a 50% inhibition of c-AMP breakdown) was calculated by interpolating 2 values of inhibition ranging from 35 to 75% against the logarithm of the dose of the flavonoid added. The I-50 values of the most important dimeric flavonoids in this test are reported in Table II.

TABLE II

| | I-50 Values | |
| | $I_{50}$ | |
| Substances | Cyclic AMP | Cyclic GMP |
|---|---|---|
| Amentoflavone | 0.65 | 0.58 |
| Ginkgonetine | 0.88 | 0.49 |
| Ginkgo/Flav. | 2.46 | 1.85 |
| Papaverine | 5.00 | 12.44 |
| Cromoglycate Na | 2000 | 235 |

Assays were performed with 1 µM substrate, $I_{50}$ was calculated as described above.

In the treatment of undesirable aestethic body areas the combinations of the hydroalcoholic extracts of *Ipomea hederacea* with the extracts of *Ginkgo biloba* enriched in dimeric flavones or the extracts of *Salvia meltiorrhiza* with the extracts of *Ginkgo biloba* or *Selaginella rupestris* were particularly interesting. To reduce fat deposits, the treatment with the above cited extracts must be continued for a few days or weeks depending on the seriousness of the unattractiveness.

The dosage of the extracts or of the pure active constituents of the plants having adenylate-cyclase agonistic or antiphosphodiesterase action or alpha-2-adrenergic receptor blocking action such as α-yohimbine, may vary between 0.1 mg to 0.2 mg; these products in form of extracts or pure constituents may be incorporated in formulations containing the usual excipients, such as those reported in the Remington's Pharmaceutical Sciences Handbook, Mack Pub. Co., N.Y., U.S.A. Particularly preferred excipients are both natural or synthetic phospholipids which increase the absorption of the active principles through the skin. The daily posology of the active ingredients in the formulations depends on the patient's conditions and on the seriousness of the pathology and can be divided in two or more administrations per day. Normally a complete cycle of therapy takes, in combination with a proper diet, a treatment of 10 to 180 days.

The active principles of the compositions of the invention are prepared by extracting the vegetable material with alcohols or aliphatic ketones either alone or in admixture with water or, when the active principles are lipophilic, with aromatic and/or aliphatic hydrocarbons or with ethyl acetate. The obtained extracts may be purified from inert or undesired substances by partitioning the active principles between an aqueous phase and selective solvents. An alternative process for the purification of said extracts comprises the adsorption on resins when the extracts are obtained by aqueous extraction or with water miscible solvents.

The adsorbed active principles may be selectively released from the resin using solvents with different polarity or high dielectric constant. The resins used for these separations are usually those having polystyrene matrix, such as Amberlites (R) and Duolites (R).

Duolite S-730$^R$ and Amberlite XAD2$^R$ are preferably used.

According to the latter process, the active principles of *Salvia meltiorrhiza* and of other plants belonging to the Labiatae family may be selectively eluted using toluene/ethyl acetate mixtures preferably in the 8:2 ratio; the active principles of *Ipomea species* are preferably extracted from aqueous solutions after acidification at pH around 1.5 with n-butanol or mixture of n-butanol and toluene; the extracts obtained according to the above cited procedures can be directly incorporated in cosmetic or pharmaceutical formulations and used in human medication.

As far as the anti-phosphodiesterase principles are concerned, the methods employed for their preparation are those normally used for dimeric flavones.

The following examples are given by way of illustration of the present invention.

EXAMPLE 1

Preparation of *Ipomea hederacea* extract.

100 g of *Ipomea hederacea* seeds are ground and extracted several times with 400 ml of a mixture of ethanol/water 6:4 (v/v); to eliminate drug impurities and flocculated materials, the combined extracts are filtered and then concentrated under vacuum to dryness; 14 g of brown solid were obtained which are ready for biological application.

EXAMPLE 2

Preparation of *Salvia meltiorrhiza* purified extract.

500 g of *Salvia meltiorrhiza* roots are ground and extracted 5 times with 2 l of a mixture of ethanol/water 1:1; to eliminate drug impurities the combined extracts are filtered and then concentrated under vacuum to 500 ml (extract/drug ratio 1:1 v/w); the cloudy suspension is extracted four times with 500 ml of ethylacetate; the organic phase after filtration on $Na_2SO_4$ is concentrated under vacuum to dryness. 2 g of a red extract enriched in tanshinone like substance were obtained; this purified extract, poorly soluble in water can be incorporated in oily emulsions alone for the treatment of fatty unattractiveness.

EXAMPLE 3

Preparation of purified extract of *Salvia officinalis*.

500 g of leaves and stems of *Salvia officinalis* are steam distilled to remove the essential oils; after distillation the drug is continuously extracted with alcohol until exhaustion. The solvent is concentrated under vacuum to 500 ml and the aqueous residue extracted twice with 300 ml of ethyl acetate and the organic phase concentrated to dryness. The residue containing chlorophyll and other inert substances was solubilized in alcohol extracted with n-hexane; the alcoholic phase after concentration to dryness represents the active fraction of *Salvia officinalis*.

EXAMPLE 4

Preparation of dimeric flavonoids mixture from *Ginkgo biloba* leaves.

500 g of green *Ginkgo biloba* leaves are extracted with methanol until exhaustion of the solvent is concentrated to small volume and the residue diluted with 100 ml of a mixture of methanol/water 1:1, this phase is extracted twice with 100 ml of chloroform. The chloroform solution is evaporated under vacuum to dryness and the residue, solubilized in 100 ml of methanol/water 60% is extracted with n-hexane. The hexane extract is eliminated while the aqueous methanol is concentrated to dryness. This residue contains about 40% of dimeric flavonoids with amentoflavone skeleton and can be used as an active ingredient in formulations useful fat deposits reduction.

EXAMPLE 5

Preparation of a cream containing as active ingredients *Salvia metiorrhiza* extract, *Ginkgo biloba* dimeric flavonoids fraction and *alpha-Yohimbine*.

Each 100 g cream contains:

| | |
|---|---|
| Salvia meltiorrhiza extract (example 2) | 0.2 g |
| Ginkgo biloba dimeric flavonoids (example 4) | 0.2 g |
| Alpha Yohimbine | 0.05 g |
| Soybean Phospholipids | 2.00 g |
| Carboxyvinylpolymer (Carbomer 934) | 1.2 g |
| Sodium lauryl sarcasinate | 0.5 g |
| Polysorbate 80 | 3 g |
| Hydrogenated lanolin | 5 g |
| Spermaceti | 5 g |
| Polyisoprene | 5 g |
| Wheat Oil | 2 g |
| Dimethylsilicone oil | 0.5 g |
| Triton 80 | 0.1 g |
| Parfum | 0.3 g |
| 10% Sodium hydroxide sol | 2 g |
| Water | q.s. 100 g |

What is claimed is:

1. A topical pharmaceutical composition for the treatment of superfluous fat deposits in which the active components consist essentially of a combination in a weight ratio of 1:2 to 2:1 of (a) at least one component of *Salvia meltiorrhiza* having adenylate cyclase agonistic activity and (b) at least one component of *Ginkgo biloba* having antiphosphodiesterase activity, said combination being present in an effective amount and admixed with at least one topically acceptable pharmaceutical excipient.

2. A pharmaceutical composition according to claim 1 wherein the component of *Ginkgo biloba* is a flavone dimer.

3. A pharmaceutical composition according to claim 2 wherein the flavone dimer is amentoflavone or bilobetaine.

4. A pharmaceutical composition according to claim 1 wherein the pharmaceutical excipient includes a phospholipid.

5. The method of treating superfluous fat deposits in a human which comprises topically applying an effective amount of a combination of (a) at least one component of *Salvia meltiorrhiza* having adenylate cyclase agonistic activity and (b) at least one component of *Ginkgo biloba* having antiphosphodiesterase activity.

6. The method according to claim 5 wherein the component of Ginkgo biloba is a flavone dimer.

7. The method according to claim 5 wherein the flavone dimer is amentoflavone or bilobetaine.

* * * * *